US009187268B2

(12) United States Patent
Denninger et al.

(10) Patent No.: US 9,187,268 B2
(45) Date of Patent: Nov. 17, 2015

(54) LABORATORY SAMPLE DISTRIBUTION SYSTEM AND CORRESPONDING METHOD OF OPERATION

(71) Applicant: Roche Diagnostics Operations, Inc., Indianapolis, IN (US)

(72) Inventors: Oliver Denninger, Karlsruhe (DE); Michael Heise, Marbach (DE); Hans Schneider, Schwaikheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/263,034

(22) Filed: Apr. 28, 2014

(65) Prior Publication Data

US 2014/0231217 A1 Aug. 21, 2014

(30) Foreign Application Priority Data

Nov. 4, 2011 (EP) .................................. 11187972

(51) Int. Cl.
*B65G 54/02* (2006.01)
*G01N 35/04* (2006.01)
(Continued)

(52) U.S. Cl.
CPC ................. *B65G 54/02* (2013.01); *B65G 43/00* (2013.01); *G01N 1/00* (2013.01); *G01N 35/04* (2013.01); *B65G 2201/0261* (2013.01); *G01N 2035/0477* (2013.01)

(58) Field of Classification Search
CPC ................... B65G 54/02; B65G 43/00; B65G 2201/0261; G01N 1/00; G01N 35/04; G01N 2035/0477
USPC .................... 198/619, 465.1, 358; 422/63, 65
See application file for complete search history.

(56) References Cited

U.S. PATENT DOCUMENTS

| 3,273,727 A | 9/1966 | Rogers et al. |
| 3,653,485 A | 4/1972 | Donlon |

(Continued)

FOREIGN PATENT DOCUMENTS

| CN | 201045617 Y | 4/2008 |
| DE | 3909786 A1 | 9/1990 |

(Continued)

OTHER PUBLICATIONS

International Search Report issued Dec. 12, 2012, in Application No. PCT/EP2012/071751, 4 pages.

*Primary Examiner* — Mark A Deuble
(74) *Attorney, Agent, or Firm* — Roche Diagnostics Operations, Inc.

(57) ABSTRACT

A laboratory sample distribution system is presented. The system comprises a plurality of container carriers. The container carriers each comprise at least one magnetically active device such as, for example, at least one permanent magnet, and carry a sample container containing a sample. The system also comprises a transport device. The transport device comprises a transport plane to carry the plurality of container carriers and a plurality of electro-magnetic actuators stationary arranged below the transport plane. The electro-magnetic actuators move a container carrier placed on top of the transport plane by applying a magnetic force to the container carrier. The transport device also comprises a control device to control the movement of the container carriers on top of the transport plane by driving the electro-magnetic actuators. The control device controls the movement such that more than two container carriers are movable simultaneously and independently from one another.

16 Claims, 6 Drawing Sheets

(51) Int. Cl.
  *B65G 43/00*  (2006.01)
  *G01N 1/00*  (2006.01)

(56) References Cited

U.S. PATENT DOCUMENTS

| | | | |
|---|---|---|---|
| 5,720,377 A * | 2/1998 | Lapeus et al. | 198/346.1 |
| 5,788,929 A | 8/1998 | Nesti | |
| 6,045,319 A | 4/2000 | Uchida et al. | |
| 6,062,398 A | 5/2000 | Thalmayr | |
| 6,260,360 B1 | 7/2001 | Wheeler | |
| 7,028,831 B2 * | 4/2006 | Veiner | 198/619 |
| 7,850,914 B2 * | 12/2010 | Veiner et al. | 422/65 |
| 7,858,033 B2 | 12/2010 | Itoh | |
| 8,281,888 B2 | 10/2012 | Bergmann | |
| 2003/0089581 A1 | 5/2003 | Thompson et al. | |
| 2004/0050836 A1 | 3/2004 | Nesbitt et al. | |
| 2005/0061622 A1 | 3/2005 | Martin | |
| 2005/0196320 A1 | 9/2005 | Veiner et al. | |
| 2007/0210090 A1 | 9/2007 | Sixt et al. | |
| 2008/0286162 A1 | 11/2008 | Onizawa et al. | |
| 2009/0322486 A1 | 12/2009 | Gerstel | |
| 2010/0000250 A1 | 1/2010 | Sixt | |
| 2010/0175943 A1 | 7/2010 | Bergmann | |
| 2010/0312379 A1 | 12/2010 | Pedrazzini | |
| 2012/0275885 A1 | 11/2012 | Furrer et al. | |
| 2013/0034410 A1 | 2/2013 | Heise et al. | |
| 2013/0126302 A1 * | 5/2013 | Johns et al. | 198/439 |
| 2013/0263622 A1 | 10/2013 | Mullen et al. | |
| 2013/0322992 A1 | 12/2013 | Pedrazzini | |
| 2015/0233956 A1 | 8/2015 | Buehr | |
| 2015/0233957 A1 | 8/2015 | Riether | |

FOREIGN PATENT DOCUMENTS

| | | |
|---|---|---|
| DE | 102011090044 A1 | 7/2013 |
| EP | 0601213 A1 | 10/1992 |
| EP | 0775650 A1 | 5/1997 |
| EP | 0896936 A1 | 2/1999 |
| GB | 2165515 A | 4/1986 |
| JP | S61-217434 A | 9/1986 |
| JP | H02-87903 A | 3/1990 |
| JP | 6-156730 A | 6/1994 |
| JP | H11-304812 A | 11/1999 |
| JP | 3112393 A | 9/2000 |
| JP | 2001-240245 A | 9/2001 |
| JP | 2005-249740 A | 9/2005 |
| JP | 2009-300402 A | 12/2009 |
| SU | 685591 A1 | 9/1979 |
| WO | 03/042048 A3 | 5/2003 |
| WO | 2007/024540 A1 | 3/2007 |
| WO | 2010/129715 A1 | 11/2010 |
| WO | 2011/138448 A1 | 11/2011 |
| WO | 2012/158541 A1 | 11/2012 |

* cited by examiner

| | | | | | |
|---|---|---|---|---|---|
| t=0 | 5_1=OFF | 5_2=ON | 5_3=OFF | 5_4=OFF | 5_5=OFF |
| t=1 | 5_1=OFF | 5_2=OFF | 5_3=ON | 5_4=OFF | 5_5=OFF |
| t=2 | 5_1=OFF | 5_2=OFF | 5_3=OFF | 5_4=ON | 5_5=OFF |

LABORATORY SAMPLE DISTRIBUTION SYSTEM AND CORRESPONDING METHOD OF OPERATION

CROSS-REFERENCE TO RELATED APPLICATIONS

This application is a continuation of PCT/EP2012/071751, filed Nov. 2, 2012, which is based on and claims priority to EP 11187972.2, filed Nov. 4, 2011, which are hereby incorporated by reference.

BACKGROUND

The present disclosure generally relates to a laboratory sample distribution system and a corresponding method of operation.

Laboratory sample distribution systems are used to distribute samples or specimens, for example, blood samples or specimens, between various different laboratory stations or specimen-processing instruments, such as pre-analytical stations, analytical stations and post-analytical stations.

In one prior art system, a drive mechanism which operates to advance specimen-container racks on a surface by producing an X/Y movable magnetic field below the surface. The movable magnetic field is produced by permanent magnets carried by an X/Y movable magnetic truck assembly. The magnetic field produced by each magnet magnetically couples with magnetically-attractive members carried in a base portion of each specimen-transport rack. The magnetic bond between the magnets and magnetically-attractive members is sufficiently strong that, as the magnetic truck assembly moves in the X/Y plane, a magnetically-coupled rack follows. Due to mechanical constraints caused by the X/Y movable magnetic truck assembly independent simultaneous movements of multiple specimen-transport racks are difficult to implement. Further, specimen-containers can only be moved together in specimen-transport rack quantities.

Therefore, there is a need to provide a laboratory sample distribution system and a corresponding method of operation that is highly flexible and offers a high transport performance.

SUMMARY

According to the present disclosure, a laboratory sample distribution system and method are presented. The laboratory sample distribution system can comprise a plurality of container carriers. Each container carrier can comprises at least one magnetically active device and carries a sample container containing a sample. A transport device can comprise a transport plane to carry the plurality of multiple container carriers and a plurality of electro-magnetic actuators stationary arranged below the transport plane. The electro-magnetic actuators can move a container carrier placed on top of the transport plane by applying a magnetic force to the container carrier. The transport device can also comprise a control device to control the movement of the container carriers on top of the transport plane by driving the electro-magnetic actuators. The control device can control the movement such that two or more container carriers can be movable simultaneously and independently from one another.

Accordingly, it is a feature of the embodiments of the present disclosure to provide a laboratory sample distribution system and a corresponding method of operation that is highly flexible and offers a high transport performance. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample or specimen distribution system according to a first embodiment can comprise a plurality of container carriers such as, for example about 50 to about 500 container carriers. The container carriers cannot be self-powered. The container carriers can comprise at least one magnetically active, i.e. magnetically attractive, device and can carry a single sample container.

Further, the system can comprise a transport device including a two dimensional transport plane or supporting surface which may be completely planar and can carry at least part of the container carriers. The transport device can further includes a plurality of electro-magnetic actuators, for example, about 50 to about 5000 electro-magnetic actuators, which can be arranged stationary or fixed below the transport plane. The electro-magnetic actuators can move a container carrier on top of the transport plane in at least two different directions by applying or causing a magnetic force to the container carrier, i.e. to the magnetically active device of the container carrier. The transport device can further includes a control device to control the movement of the container carriers on top of the transport plane by driving the electro-magnetic actuators, for example, with a corresponding driving current. The control device can control the movement such that more than two container carriers can be movable simultaneously and independently from one another. Simultaneously can indicate that during a certain time interval at least two container carriers move. Independently can indicate that the container carriers may be moved, for example, in different directions, with different speeds, along different paths, and starting the movement at different points in time. The control device may be incorporated as a personal computer running control software. The personal computer may interact with dedicated driving hardware physically driving the electro-magnetic actuators.

The transport plane can support the container carriers in a way to allow movement along directions as guided by magnetic forces. Accordingly, the transport plane can be continuous in at least those directions of movements to allow a smooth travel of the container carriers. In order to allow a flexible transfer of carriers along many lateral directions, a flat transport plane can be an advantage. On a microscopic level, it can be advantageous to employ a surface with many small protrusions in order to reduce friction between the transport plane and the bottom surface of the container carrier.

The transport plane can further transmit the magnetic field of the electro-magnetic actuators. Accordingly, the transport plane can be made from magnetically transmissive materials such as, for example, glass or plastics. Further, the thickness of the transport plane can be a compromise between mechanical stability and magnetic shielding. A transport plane having a thickness of about 2 to about 10 mm can be well suited.

The magnetically active device can be a device to cause magnetic forces in interaction with a corresponding magnetic field. The magnetically active device may comprise at least one permanent magnet. By the multiple electro-magnetic actuators interacting individually with corresponding container carriers, it can be possible to independently and simultaneously move multiple individual sample containers along a given grid over the transport plane offering high transport flexibility, which can mean that single containers can be transported independently from each other to desired locations on the transport plane.

The movement may be controlled such that collisions between container carriers moving simultaneously and independently from one another along different paths can be avoided. Collisions may occur if more than one container carrier tries to move to the same position or location. Collisions may be avoided by checking if a next position on a route or path of a container carrier is blocked or occupied by another container carrier moving along a different route. If the next position is blocked, the container carrier can be parked on an actual position. When the next position is free of any container carriers, the parked container carrier can continues its movement. Additionally, collisions may be logically avoided, for example, by optimizing routes avoiding collisions a priori.

The movement may be controlled such that at least one transport section can be logically defined or formed on the transport plane. Container carriers moving in a given transport section can have the same transport direction. The transport section can cluster the transport plane in logical sections. Within each transport section, the container carriers can be moved unidirectionally. Thus, each transport section can logically define a road having one or more tracks. The container carriers can move along the given tracks. Clustering the transport plane in different logical transport sections can reduce or eliminate the number of crossings between different container carrier routes. Thus, the complexity in finding routes for multiple container carriers to be moved simultaneously over the transport plane can be reduced.

Outside of the transport sections the container carriers may move in any direction technically possible. Transport sections may be visibly marked on the transport plane.

The movement may be controlled such that a route defined by a start location and a destination location can be optimized by a given criteria. The given criteria can be at least one of the group of: shortest distance between the start location and the destination location, transport time between the start location and the destination location, number of intersections with other routes, priority assigned to a container carrier, and defective electro-magnetic actuators. If the criterion is the number of intersections with other routes, the route may be planned avoiding intersections as far as possible. This can reduce dependencies between container carriers moving along different routes over the transport plane. If the criterion is the priority assigned to a container carrier, wherein two or more different priorities may be assigned, it can be possible to speed up the transport of container carriers having a higher priority. Thus, emergency samples may be moved by container carriers having the highest priority thereby minimizing the overall processing time of such emergency samples. If the criterion reflects defective electro-magnetic actuators, it can be possible to operate the transport plate even if some of the electro-magnetic-actuators are defective. A route can be planned such that those defective electro-magnetic-actuators can be circumnavigated. The positions of defective electro-magnetic-actuators may be automatically detected and/or input by an operator.

The transport plane may comprise insertion areas for manually and/or automatically placing/inserting container carriers and/or sample containers on the transport plane.

A bar code reader and/or a RFID reader may be placed adjacent or within the insertion area so that barcodes and/or RFID tag information identifying samples/sample containers actually placed on the insertion area may be read and further processed by the control device.

Accordingly, the transport plane may comprise removal areas for manually and/or automatically removing container carriers and/or sample containers from the transport plane.

The transport plane may be covered such that only the insertion areas and the removal areas can be accessible by a user to prevent unwanted manipulation.

For samples comprised in sample containers which need to be analyzed in short time (STAT samples or priority samples) dedicated priority insertion areas and removal areas on the transport plane may be provided. Container carriers carrying such priority samples can be placed on the priority insertion area manually or by a device. After being placed on the priority insertion area, the container carriers can be moved over the transport plane with priority under the control of the control device.

A priority assignment to a sample container and to the corresponding container carrier may be performed simply by placing the container carrier carrying the priority sample on the priority insertion area. Sensor devices, for example, a barcode reader and/or an RFID reader, may detect the presence of a container carrier and may determine all necessary information for further processing and transfer this information to the control device.

Additionally or alternatively, priority assignment may be performed by the control device having knowledge of sample containers to be processed/moved with priority. If the sample container having priority is placed in a container carrier, the control device may control the prioritized movement of the container carrier over the transport plane.

The system may further comprise a container carrier sensing device to sense the presence and/or position of container carriers located on the transport plane. A scheduled position of a container carrier, i.e. a position a container can have if the system works without fault according to the scheduling by the control device and a sensed position of a container carrier can be compared. If the scheduled position does not match with the sensed position, an error message may be generated. Alternatively, the transport device may be stopped so that all container carriers stop moving. This can allow for a secure operation of the system since fault conditions can be detected and handled safely.

By comparing the scheduled position and the sensed position it is further possible to for example detect a gradual reduction of the transport speed, for example, caused by contamination of the transport plane resulting in an increased friction. If such a gradual reduction of the transport speed is determined, the control device may accordingly increase the magnetic force generated by the electro-magnetic actuators and/or display an error message if the transport speed is below a given threshold.

When powering down, for example, in the case of an electrical power outage, the actual sensed positions/status may be stored by the control device. The stored positions/status may be used by the control device when powering up again. The control device may compare the stored positions with actually sensed positions. In the case of a mismatch, the control device may generate an error message and/or perform an error procedure.

It can be self-evident that an uninterrupted power supply may be used to provide sufficient electrical power for powering down safely in the case of an electrical power outage.

The transport plane may comprise one or more displays, for example, LEDs, indicating the status of the transport plane. LEDs may, for example, be arranged below translucent areas of the transport plane. The LEDs can indicate the status, for example, by flashing, of a corresponding electro-magnetic actuator, the position of a specific container carrier, areas to be cleaned, insertion/removal areas, defective areas, and the like.

The transport plane may comprise at least one transfer area located adjacent to a laboratory station (also called laboratory device) and/or an automatic transfer device. The transfer area may store a plurality of container carriers for sequentially processing by the laboratory station or the automatic transfer device. The transfer area may comprise a handover position, wherein container carriers exclusively enter the transfer area by passing the handover position. The transfer area can provide a dynamic processing queue for a corresponding laboratory station, thereby enabling a flexible load balancing. The dynamic processing queue may get longer if a large number of samples have to be processed by the corresponding laboratory station having a limited processing capacity. The non-processed sample carriers or samples can be queued at locations within the transfer area, wherein the number of locations may be fixed or variable. If the number is variable, the size of the transfer area may be dynamically increased in response to the number of container carriers waiting for processing. The fixed handover position can simplify routing to a laboratory station, since in every case the destination i.e. the handover position can be known.

The system may comprise a visualizing device to visualize the presence and position of container carriers located on the transport plane; and/or the presence and position of sample containers located on the transport plane such as, for example, including information regarding corresponding samples; and/or error conditions of the sample distribution system. An error condition may for example be a defective electro-magnetic actuator. The visualizing device may for example be a LCD monitor. Using the visualizing device, it can be possible to visually supervise the operation of the system and to handle complex error conditions by visually guided manually interacting.

A method for the versatile transport of sample containers can be achieved with a laboratory sample distribution system comprising a plurality of container carriers. The system can comprise a transport device for moving the container carriers. The transport device can comprise a transport plane to carry the plurality of container carriers, a plurality of electro-magnetic actuators arranged below the transport plane, the electro-magnetic actuators can move a container carrier placed on top of the transport plane by applying a magnetic force to the container carrier, and a control device to control the movement of the container carriers on top of the transport plane. The movement of the container carriers on top of the transport plane can be controlled by driving the electro-magnetic actuators such that two or more container carriers can be movable simultaneously and independently from one another. The term "simultaneously" can herein mean that at least at certain time intervals the two container carriers can both be in motion.

The at least one permanent magnet may be ball-shaped. A north pole or a south pole of the ball-shaped permanent magnet can be directed to the transport plane. In other words, an axis extending through the opposite poles of the ball-shaped permanent magnet can be perpendicular to the transport plane. A diameter of the ball-shaped permanent magnet may be approximately 12 mm. The ball-shaped permanent magnet can cause an optimized magnetic field in interaction with the electro-magnetic actuators, for example, compared with a bar magnet, resulting in higher magnetic force components in a lateral movement direction.

The permanent magnet in conjunction with a ferromagnetic core of a currently adjacent non-activated electro-magnetic actuator can cause an unwanted magnetic retention force. The retention force can hinder the desired movement of the container carrier away from the currently adjacent non activated electro-magnetic actuator towards an activated electro-magnetic actuator. Increasing the distance between the permanent magnet and the transport plane, i.e. also increasing the distance between the permanent magnet and the electro-magnetic actuators, can reduce this magnetic retention force. Unfavorably, an increasing distance can also lower a desired magnetic transport force in a lateral movement direction. Therefore, a distance between a center of the at least one permanent magnet and a bottom surface of the container carrier, the bottom surface can be in contact with the transport plane, may be selected within a range of about 5 mm to about 50 mm. The given distance range can provide an optimized compromise between a desired magnetic transport force in movement direction and an unwanted magnetic retention force.

The container carriers may comprise a first permanent magnet arranged in the center of a stand of the container carrier and a second permanent magnet having a ring shape arranged in the stand surrounding the first permanent magnet. This arrangement can provide high flexibility in causing push and pull magnetic forces, especially if more than one electro-magnetic actuator is activated at a given time. The first and second permanent magnets may have a reverse polarity, i.e. a south pole of the first permanent magnet and a north pole of the second permanent may point to the transport plane, or vice versa. The ring shaped second permanent magnet may constitute a circular area having a diameter that is smaller than a distance between axes of electro-magnetic actuators of the transport plane.

The container carriers may comprise a RFID tag storing a unique ID. This can enable matching between a sample container ID, for example, a barcode, and the corresponding container carrier. The unique carrier ID can be read by an optional RFID reader being part of the system and placed at one or more specific locations within the system.

The RFID tag may comprise a ring shaped antenna arranged in a stand of the container carrier. This antenna arrangement can make it possible to read the RFID tag by a RFID reader antenna below the transport plane. Thus, the transport plane itself and/or areas above the transport plane may be designed free of any disturbing RFID reader antennas.

A stand of the container carrier can have a circular cross section having a diameter of approximately 3.5 cm to 4.5 cm. The circular cross section of the stand can reduce the likelihood of a stand collision of container carriers moving adjacent in different directions. Compared for example with quadratic stands, this can reduce the required safety distance between adjacent positions and the requirements on positioning accuracy. Further, the circular stand can improve the self-supporting of the container carrier, for example, prevents that the containers carrier tilts under normal operating conditions.

The electro-magnetic actuators may comprise a ferromagnetic core guiding and amplifying a magnetic field. The electro-magnetic actuators may have a center finger and four outer fingers, each of the fingers extending perpendicular to the transport plane. Only the center finger may be surrounded by a coil being driven by an actuating current. This arrangement can reduce the number of coils needed for activating the electro-magnetic actuators. The center finger and the outer fingers can interact advantageously by providing push and pull forces, respectively, especially if the container carrier comprises a first permanent magnet arranged in the center of the stand and a second permanent magnet having a ring shape arranged in the stand surrounding the first permanent magnet.

The electro-magnetic actuators may be arranged in rows and columns forming a grid or matrix of active transport fields. The rows and columns can have either a first grid dimension g1 or a second grid dimension g2, wherein g2=2*g1. Adjacent rows and adjacent columns can have different grid dimensions. The grid dimension can specify a distance between adjacent or consecutive electro-magnetic actuators in a given row or column. In other words, the electro-magnetic actuators can be arranged in form of a grid or matrix, wherein the grid or matrix can have blank positions representing omitted electro-magnetic actuators. This arrangement can consider that diagonal movements of the container carriers may not be necessary to reach a specific destination on the transport plane since the specific destination can be reached based on movements along the rows and columns. The mentioned arrangement of the electro-magnetic actuators can reduce the number of required electro-magnetic actuators significantly (by e.g. 33%) compared to a solution having a constant grid dimension. Nevertheless, if a diagonal movement is required, it can be self-evident that the rows and columns may be provided having a constant grid dimension, for example, forming a transport plane being divided in active transport fields with equal dimensions.

The transport plane may be divided into multiple sub-planes. Each sub-plane can have a first outer face, a second outer face, a third outer face and a fourth outer face at which further planes can be arranged in a tiling manner to form a transport plane. This approach can offer the ability to provide transport planes of desired shape. This can be a big advantage to serve the needs an individual laboratory might have due to the laboratory stations present or due to spatial restraints.

The approach to build the transport plane from sub-planes can be combined with the concept of rows having different grid dimensions to reduce the number of needed electro-magnetic actuators. Sub-planes can be employed where along the first and the second outer face the electro-magnetic actuators can be arranged in a first grid dimension g1 and along the third and the fourth outer face the electro-magnetic actuators can be arranged in a second grid dimension g2, wherein g2=2*g1. Multiple sub-planes can be arranged adjacent in a tiling manner to form the transport plane. Adjacent outer faces of different sub planes can have different grid dimensions.

The system may comprise a magnetizable coupling element to provide a magnetic coupling between adjacent electro-magnetic actuators. Due to the coupling element, the activated electro-magnetic actuator automatically can cause a magnetic field in the adjacent actuators having an inverse polarization. This can automatically provide respective pull and push forces even if only a single electro-magnetic actuator is activated, for example, by a corresponding activating current.

The surface of the container carriers and the surface of the transport plane may be arranged to reduce friction between the surfaces, for example, by coating the container carriers and/or the transport plane.

The system may comprise a cover profile covering the transport plane, especially covering multiple sub-planes forming the transport plane. The cover plane can be fluidtight. The cover plane can simplify the cleaning of the transport plane and can avoid disturbing gaps between adjacent sub-planes, when the transport plane is formed of multiple adjacent sub-planes. Further, the cover profile can mitigate height differences between adjacent sub-planes. The cover profile may be just overlying the transport plane or may be glued to the top surface of the sub planes to stabilize the arrangement and to prevent spacing which can reduce magnetic forces.

A method for the versatile transport of sample containers can be achieved with a laboratory sample distribution system comprising a plurality of container carriers. The container carriers can comprise at least one magnetically active device and can carry a sample container. The laboratory sample distribution system can further comprise a transport plane to carry the container carriers, and a plurality of electro-magnetic actuators stationary arranged below the transport plane. The electro-magnetic actuators can move a container carrier on top of the transport plane by applying a magnetic force to the container carrier. The method can comprise activating at least one of the electro-magnetic actuators to apply a magnetic force to a container carrier within an operating distance of the at least one activated electro-magnetic actuator. Activating an electro-magnetic actuator can mean that a magnetic field can be generated by the electro-magnetic actuator. Activating may be done by generating a driving current applied to a coil surrounding a ferromagnetic core.

A speed of a container carrier moving across the transport plane may be set by setting a period between a successive activation of adjacent electro-magnetic actuators. If this duration is set shorter, the speed can increase and vice versa. By changing the duration dynamically, a container carrier may be accelerated or slowed down.

The electro-magnetic actuators may be activated in response to a sensed position of the container carrier to be applied with the magnetic force. The electro-magnetic actuators may be activated such that a polarity of the generated magnetic field can depend on a position of the container carrier relative to the electro-magnetic actuator. This can cause position-depended pull and push forces. In a first position range when the container carrier is moving towards the activated electro-magnetic actuator, the pull force may attract the container carrier towards the activated electro-magnetic actuator. In a second position range when the container carrier has traversed the electro-magnetic actuator, the push force may push the container carrier away from the activated electro-magnetic actuator now generating a magnetic field having an opposite polarity. Additionally, the magnetic field strength may be changed in response to the sensed position to provide a steady movement of the container carrier. The electro-magnetic actuators may generate magnetic fields having only a single polarity to simplify the system. In this case, the activated electro-magnetic actuator may generate the pull force in the first position range when the container carrier is moving towards the activated electro-magnetic actuator. In the second position range when the container carrier has traversed the electro-magnetic actuator, the electro-magnetic actuator may be deactivated.

For moving a first container carrier along a first transport path, a first group of electro-magnetic actuators may be activated along the first transport path. For independently and at least partially simultaneously moving a second container carrier along a second transport path, a second group of multiple electro-magnetic actuators may be activated along the second transport path. Simultaneously can indicate that during a certain time interval both the first and the second container carrier move. The electro-magnetic actuators of the first or the second group may be activated one after the other along the respective transport path. Alternatively, two or more adjacent electro-magnetic actuators along the respective transport path may be activated at least partially overlapping in time.

A movement of a container carrier placed on a field on top of a first electro-magnetic actuator to an adjacent field on top of a second electro-magnetic actuator may comprise activating the first and the second electro-magnetic actuator and a third electro-magnetic actuator adjacent to the first electro-magnetic actuator and opposite to the second electro-magnetic actuator and part of the same row or column as the first and the second electro-magnetic actuators in a predetermined order.

If the container carriers comprise a first permanent magnet arranged in the center of a stand of the container carrier and a second permanent magnet having a ring shape arranged in the stand surrounding the first permanent magnet, the method may further comprise activating the second electro-magnetic actuator such that a resulting pull-force regarding the second permanent magnet having a ring shape can be generated, and activating the third electro-magnetic actuator such that a resulting push-force regarding the second permanent magnet can be generated; after a predetermined time interval or at a predetermined position of the container carrier: activating the first electro-magnetic actuator such that a resulting pull-force regarding the second permanent magnet can be generated and that a resulting push-force regarding the first permanent magnet can be generated; and after a second predetermined time interval or at a second predetermined position of the container carrier: activating the second electro-magnetic actuator such that a resulting pull-force regarding the second permanent magnet can be generated. A movement between adjacent electro-magnetic actuators can be done in a sequence of three activation patterns regarding three adjacent electro-magnetic actuators. This can lead to a continuous uniform movement with a high positioning accuracy. The first and second time interval or the first and the second position may be determined based on a sensed position of the container carrier provided by the container carrier sensing device.

Figure 1:
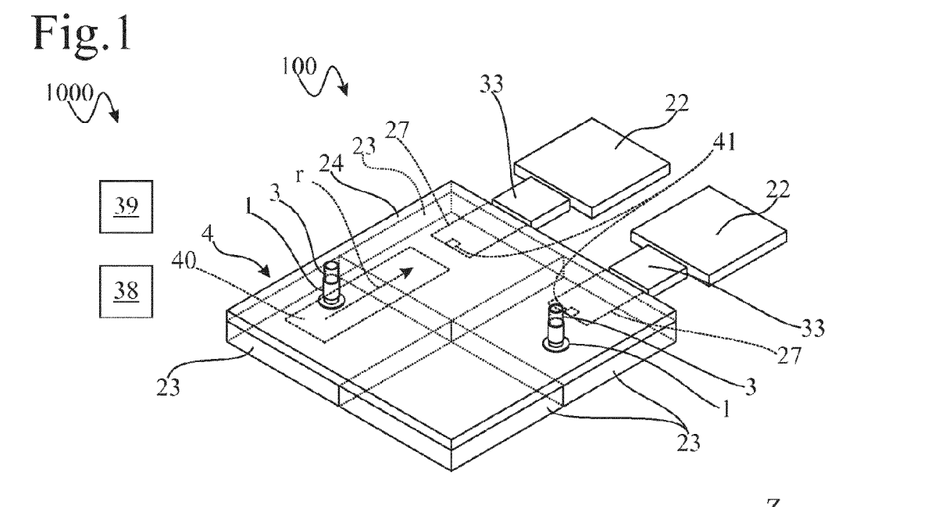
FIG. 1 illustrates a laboratory sample distribution system having a transport plane formed by multiple sub-planes according to an embodiment of the present disclosure.

Referring initially to FIG. 1, FIG. 1 shows a laboratory sample distribution system 100. The laboratory sample distribution system 100 can be used to distribute samples or specimens, e.g. blood samples, contained within sample containers or sample tubes 3 between different laboratory stations or specimen-processing instruments 22, such as pre-analytical stations, analytical stations and post-analytical stations typically used in laboratory systems.

The laboratory sample distribution system 100 can comprise a number of container carriers or Single-Tube-Carriers 1 each carrying a corresponding sample container 3 over a transport plane 4.

In order to move the container carriers 1, a transport device can be provided. The transport device can comprise the transport plane 4, electro-magnetic actuators 5 (see FIGS. 2 and 3) and a control device 38 to control the movement of the container carriers on top of the transport plane.

The control device may be incorporated as a personal computer running corresponding control software. The personal computer may interact with dedicated driving hardware (not shown) physically driving the electro-magnetic actuators 5. The physically driving may be done by applying a driving current to a coil of an electro-magnetic actuator 5.

The electro-magnetic actuators 5 can be stationary arranged below the transport plane 4. Each of the electro-magnetic actuators 5 can move a container carrier 1 in operating distance of a corresponding electro-magnetic actuator 5 by applying a magnetic force to the container carrier 1.

The depicted transport plane 4 can be divided into four quadratic sub-planes 23, the sub-planes 23 can be adjacent to one another. The transport plane can be covered by an optional cover profile 24. The cover profile 24 can be fluidtight and can cover gaps and mitigate height differences between adjacent sub-planes 23. The material of the cover profile 24 can provide a low friction coefficient. The cover profile 24 may, for example, be a glass plate or a foil of polyethylene or PTFE (poly-tetra-fluoro-ethylene).

Due to the electro-magnetic actuators 5 which may generate magnetic fields simultaneously and independently from one another, it can be possible to move multiple container carriers 1 simultaneously and independently from one another along different transport paths or routes.

The simultaneous movement of the container carriers 1 can be controlled such that collisions can be avoided. Collisions may occur if more than one container carrier 1 tries to move to the same position or location. A position may be defined by a corresponding electro-magnetic actuator 5 and may have a size corresponding to a region on the transport plane covered by a container carrier 1.

Collisions may be avoided by checking if a next position on a route or path of a container carrier 1 is blocked or occupied by another container carrier 1 moving along a different route. If the next position is blocked, the container carrier 1 can be parked on an actual position. When the next position is free of any container carriers, the parked container carrier can continue its movement.

The movement may be controlled such that at least one transport section 40 can be defined on the transport plane 4. Container carriers 1 moving in a given transport section can have the same transport direction r. The transport section 40 can cluster the transport plane 4 in logical sections. Within each transport section, the container carriers can be moved unidirectionally. Thus, each transport section can logically define or reserve a road having one or more tracks. The container carriers can move along the given tracks. Although only a single transport section 40 is depicted, it can be self-evident that more than a single transport section can be provided, each transport section having a specific transport direction. By using four transport sections combined to form a rectangle, it can be possible to simulate a conveyor, the conveyor having increased flexibility compared with a conventional conveyor.

The movement may be controlled such that a route defined by a start location and a destination location can be optimized by a given criteria. If a container carrier has to be moved between different laboratory stations 22 in order to perform a set of analyses, a start location may be a location the container carrier 1 is initially placed on the transport plane 4. The destination location may be a location adjacent to a laboratory station 22 performing a first processing step. After the first processing step has finished, a next route can be defined by a new start location corresponding to the destination location of the previous route and a destination location corresponding to a laboratory station 22 performing a next processing step.

The given criteria can be at least one of the group consisting of: shortest distance between the start location and the destination location, transport time between the start location and the destination location, number of intersections with other routes, priority assigned to a container carrier, and defective electro-magnetic actuators.

The transport plane 4 may comprise at least one logical transfer area 27 located adjacent to a laboratory station 22 and/or an automatic transfer device 33. The automatic transfer devices 33 can be arranged to automatically transfer a sample item. The sample item can be a container carrier, a sample container, part of the sample and/or the complete sample, between the transport plane 4 and a laboratory station 22.

The transfer area 27 may store a plurality of container carriers 1 for sequentially processing by the laboratory station 22 or the automatic transfer device 33. The transfer area 27 may comprise a handover position 41. Container carriers 1 can exclusively enter the transfer area 27 by passing the handover position 41. The transfer area can provides a dynamic processing queue for a corresponding laboratory station, thereby enabling a flexible load balancing.

The system may further comprise a visualizing device 39 to visualize the presence and position of container carriers 1 located on the transport plane 4; and/or the presence and position of sample containers 3 located on the transport plane such as, for example, including information regarding corresponding samples; and/or error conditions of the sample distribution system.

Figure 3:
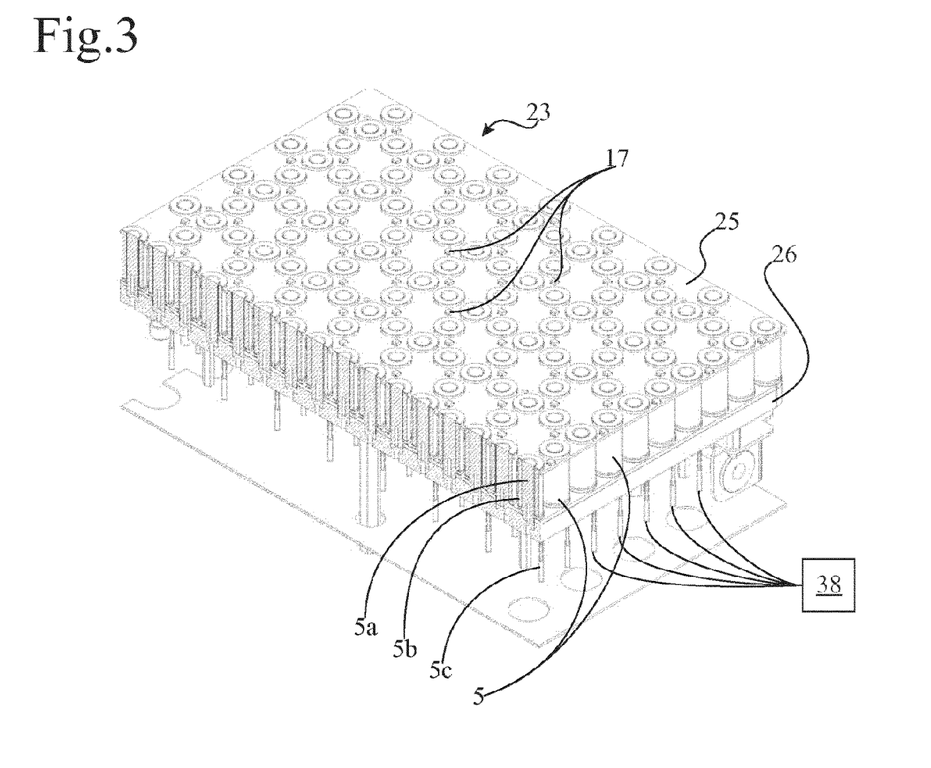
FIG. 3 illustrates a detailed perspective side view of the sub-plane shown in FIG. 2 according to an embodiment of the present disclosure.

Referring to FIG. 3 a container carrier sensing device can be provided comprising a printed circuit board 25 having multiple IR based reflection light barriers 17 arranged in a grid on top. The container carrier sensing device can sense the presence and/or position of container carriers 1 located on the transport plane 4. The IR based reflection light barriers 17 can detect container carriers 1 placed on top of a corresponding light barrier 17 since the container carriers 1 can be arranged to reflect IR radiation emitted by the light barriers 17. If no container carrier is present, no reflected IR light can get into the IR sensor of a corresponding light barrier 17.

Alternatively or additionally to the IR based reflection light barriers 17, all kind of suitable sensors, for example, magnet/hall sensors, may be used to sense the presence and/or position of container carriers 1 located on the transport plane 4.

In order to supervise the correct function of the system, a scheduled position of a container carrier 1, i.e. a position a container can have if the system works without fault, and a sensed position of a container carrier may be compared. If the scheduled position does not match with the sensed position an error message may be generated.

Figure 2:
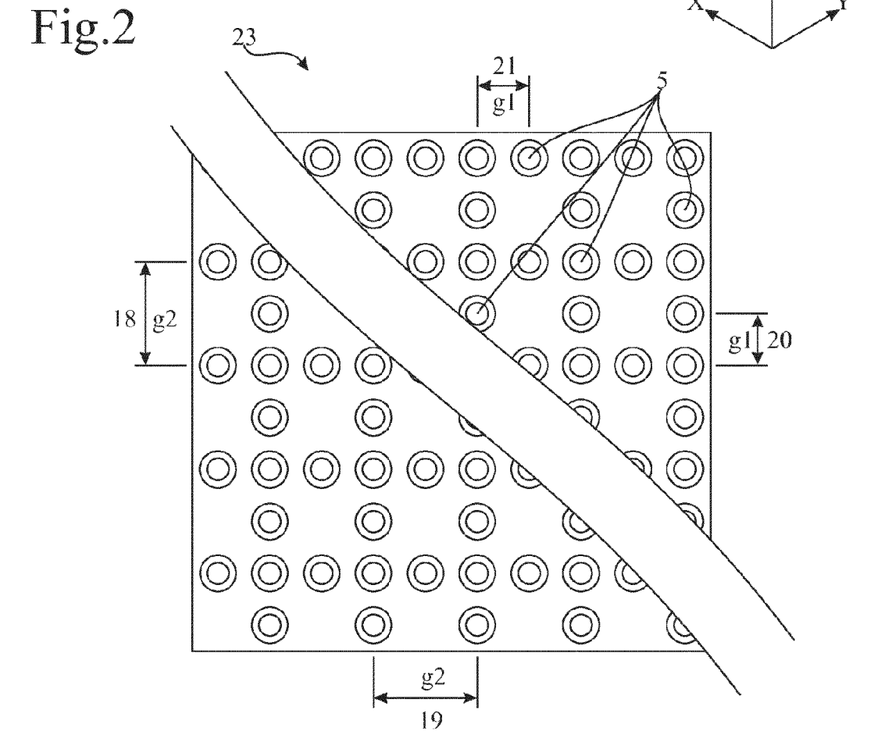
FIG. 2 illustrates a top view of an exemplary sub-plane shown in FIG. 1 according to an embodiment of the present disclosure.

FIG. 2 shows a schematic top view on an exemplary sub-plane 23 of FIG. 1. The sub-plane can have a first outer face 20, a second outer face 21, a third outer face 18 and a fourth outer face 19. Along the first and the second outer face 20 and 21, the electro-magnetic actuators 5 can be arranged in a first grid dimension g1. Along the third and the fourth outer face 18 and 19, the electro-magnetic actuators 5 can be arranged in a second grid dimension g2, wherein g2=2*g1. The grid dimension g1 may for example be about 20 mm.

The electro-magnetic actuators 5 can be arranged in rows and columns, for example, 16 rows and 16 columns, the rows and columns having either a first grid dimension g1 or a second grid dimension g2, wherein g2=2*g1, and adjacent rows having a different grid dimension and adjacent columns having a different grid dimension. If a position or field on the transport plane has to be accessible as a target destination, a corresponding electro-magnetic actuator can be provided below that target destination. If a specific field or area needs not to be accessible, an electro-magnetic actuator may be omitted at that position.

FIG. 3 shows a detailed perspective side view of the sub-plane 23 shown in FIG. 2. As illustrated, each electro-magnetic actuator 5 can be fixed on a carrier plate 26 and can comprise a ferro-magnetic cylindrical core 5a extending substantially perpendicular to the transport plane 4. A coil 5b can surround the ferro-magnetic cylindrical core 5a. The coil 5b can be applied with an actuating current provided by the control device 38 over electrical contacts 5c. If driven by an actuating current, each electro-magnetic actuator 5 can generate a magnetic field. When this field interacts with a permanent magnet 2 (see FIG. 4) arranged in the container carrier 1, it can provide a driving force moving the container carrier 1 along the transport plane 4. The ferro-magnetic cylindrical core 5a can bundle and amplify the magnetic field generated by the coil 5b.

In the most simple form, each container carrier 1 may be exposed to a driving force generated by a single activated electro-magnetic actuator 5 proximate to the corresponding container carrier 1 thereby pulling the container carrier 1 towards the activated electro-magnetic actuator 5. Further, it can be possible to superpose push and pull driving forces of multiple electro-magnetic actuators 5 proximate to the corresponding container carrier 1.

Further, it can be possible to activate multiple electro-magnetic actuators 5 at the same time to move multiple different container carriers 1 independent of each other along predetermined paths over the transport plane 4.

Figure 4:
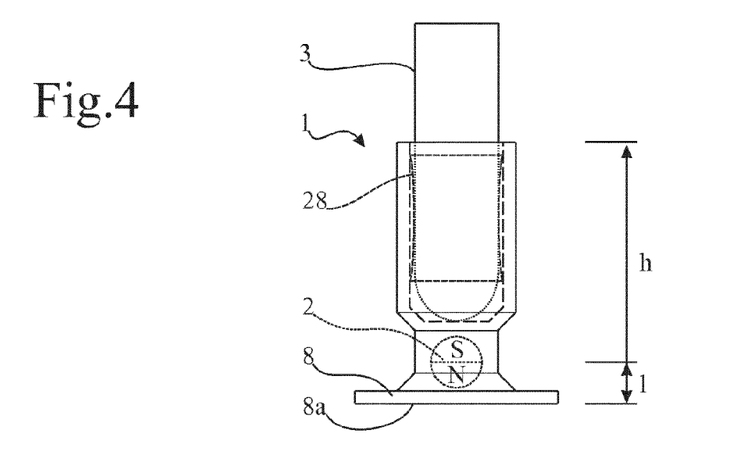
FIG. 4 illustrates a container carrier according to a first embodiment of the present disclosure.

FIG. 4 shows a container carrier 1 according to a first embodiment. The container carrier 1 can comprise a ball-shaped permanent magnet 2. A distance l between a center of the at least one permanent magnet 2 and a bottom surface 8a of the container carrier, the bottom surface 8a can be in contact with the transport plane 4, can lie within a range of about 5 mm to about 50 mm, and may be approximately 12 mm. A height h of the container carrier 1 may be approximately 42 mm.

The permanent magnet 2 may be made from hard ferromagnetic materials. These can include for example iron ore (magnetite or lodestone), cobalt and nickel, as well as the rare earth metals. A north pole N of the permanent magnet 2 can be directed towards the transport plane.

A stand 8 of the container carrier can have a circular cross section having a diameter of approximately 3.5 cm to 4.5 cm covering approximately five electro-magnetic actuators 5 if positioned in the center of a cross formed by the five electro-magnetic actuators 5. The electro-magnetic actuator in the center of the cross can be fully covered, wherein the four outer electro-magnetic actuators can be nearly covered by half. Due to this, two carriers moving on adjacent tracks can pass by each other without collision. On the other hand, the footprint can be large enough to provide a smooth transport without much tilting.

The container carriers may comprise a sample container fixer which may for example be incorporated in form of flexible flat spring 28. The flexible flat spring 28 can be arranged at the side wall of the cylindrical opening of the container carrier 3. The flexible flat spring 28 can safely fix the sample container 3 within the container carrier 1, even if the sample container 3 has a smaller diameter than the corresponding opening.

If different sample container types are used, for example, having different form factors, it can even be possible to provide specific container carriers with different inner diameters corresponding to respective sample container types.

Figure 5:
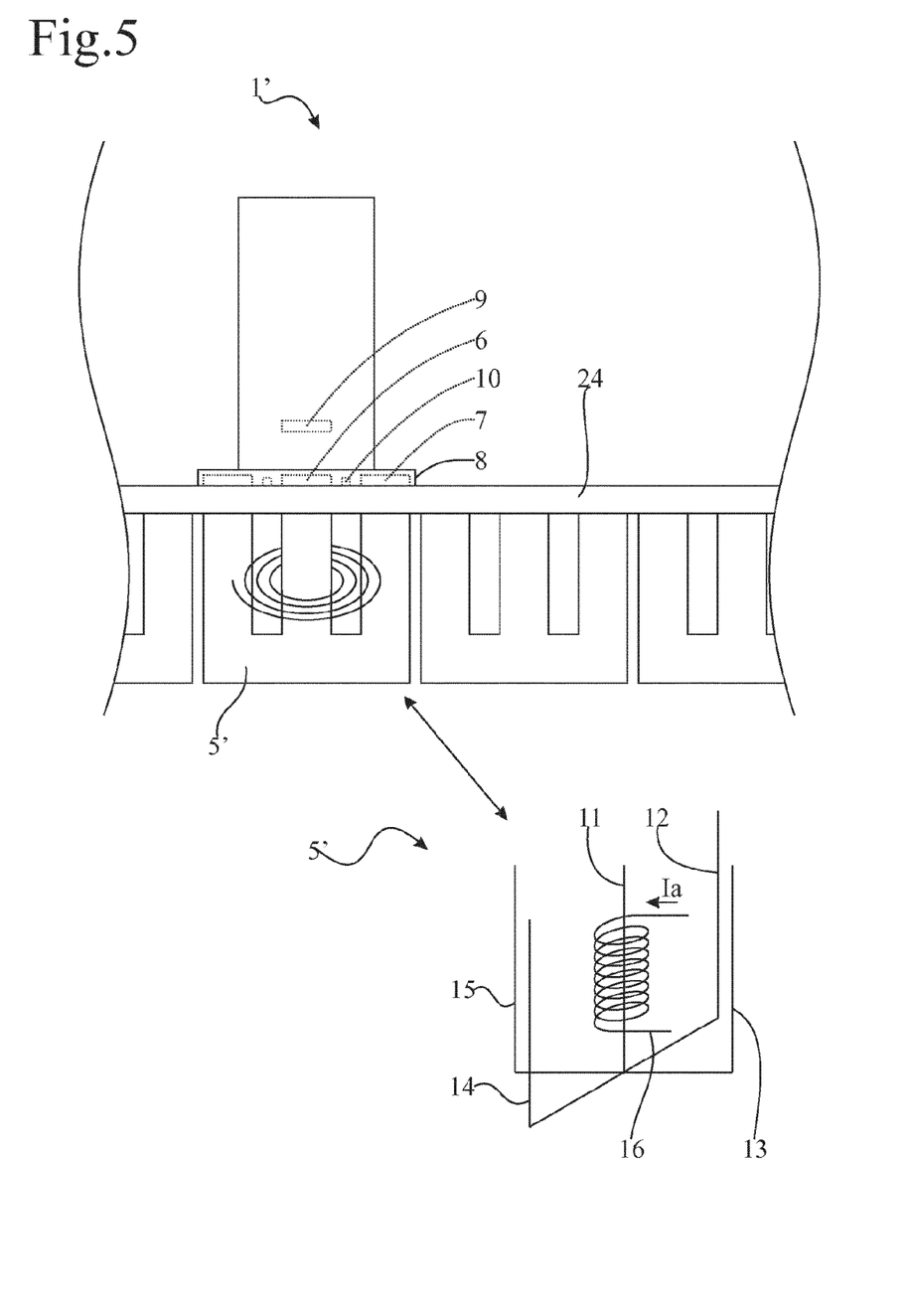
FIG. 5 illustrates a container carrier and a corresponding electro-magnetic actuator according to a second embodiment of the present disclosure.

FIG. 5 shows a container carrier 1' according to a second embodiment having a different magnet arrangement and a corresponding electro-magnetic actuator 5'. The container carrier 1' can comprise a first permanent magnet 6 arranged in the center of a stand 8 of the container carrier 1' and a second permanent magnet 7 having a ring shape arranged in the stand 8 surrounding the first permanent magnet 6. The permanent magnets 6 and 7 can have a reverse polarity. A north pole of the center permanent magnet 6 and a south pole of the ring shaped permanent magnet 7 can be directed towards the transport plane 4.

Further, the container carrier 1' can comprise a RFID tag 9 storing a unique ID corresponding to a specific container carrier. The RFID tag 9 can comprise a ring shaped antenna 10 which can be arranged in the stand 8 of the container carrier 1' between the first and the second permanent magnet 6 and 7.

The corresponding electro-magnetic actuator 5' can comprise a ferromagnetic core having a center finger 11 and four outer fingers 12, 13, 14, and 15, each of the fingers extending perpendicular to the transport plane 4, wherein only the center finger 11 can be surrounded by a coil 16 driven by an actuating current Ia. This arrangement can reduce the number of coils needed for activating the electro-magnetic actuator 5' compared with the embodiment shown in FIG. 3, wherein the center finger 11 and the outer fingers 12 to 15 can interact advantageously by providing push and pull forces, respectively, especially if the container carrier 1' is arranged as shown.

Figure 6:
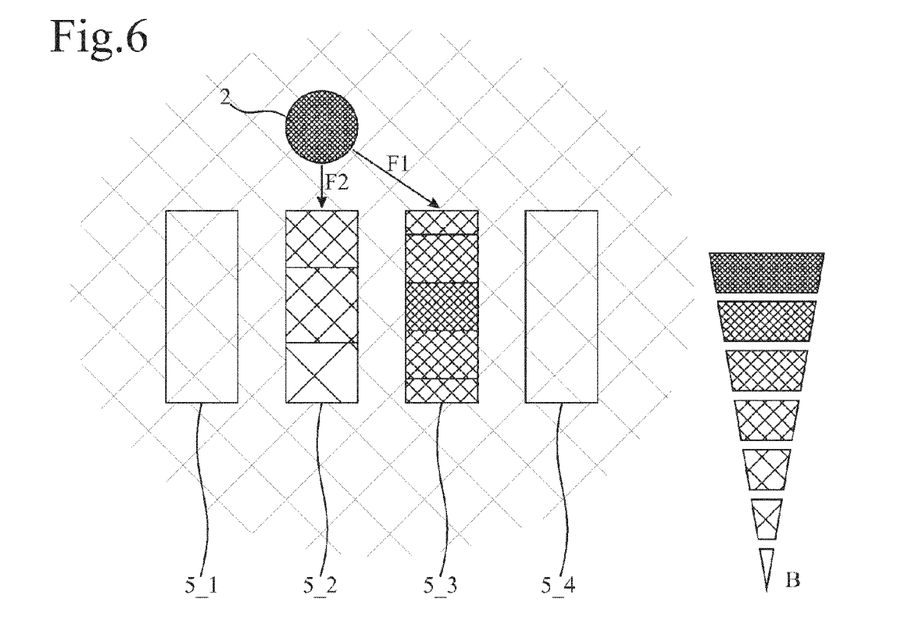
FIG. 6 illustrates a simulated magnetic flux density for a container carrier positioned on top of an electro-magnetic actuator not activated and an adjacent electro-magnetic actuator activated according to an embodiment of the present disclosure.

FIG. 6 shows a simulated magnetic flux density B for the case that a container carrier as depicted in FIG. 4 is positioned on top of an electro-magnetic actuator 5_2 not being activated and an adjacent electro-magnetic actuator 5_3 being activated. Different flux densities B can be represented by corresponding hachures. As shown, the ball shaped permanent magnet 2 in conjunction with a ferromagnetic core of the non-activated electro-magnetic actuator 5_2 can cause an unwanted magnetic retention force F2 pulling the permanent magnet 2 towards the ferromagnetic core of the non-activated electro-magnetic actuator 5_2, thereby causing an unwanted force-component in opposite direction of the desired movement and additionally increasing friction between the corresponding surfaces of the transport plane and the stand. The activated electro-magnetic actuator 5_3 can generate a force F1.

In order to reduce these unwanted effects, it can be possible to generate an opposing magnetic field by reversely activating the electro-magnetic actuator 5_2 pushing the container carrier, thereby reducing friction. Alternatively or additionally, it can be possible to choose an optimized distance between the permanent magnet 2 and the transport plane, see also the description regarding FIG. 4.

Nevertheless, the magnetic forces in a desired movement direction using a ball-shaped permanent magnet 2 can be higher compared to a bar magnet, since the resulting distances between the magnetically active spherical surface of the permanent magnet 2 and the active electro-magnetic actuator 5_3 can be smaller.

Figure 7:
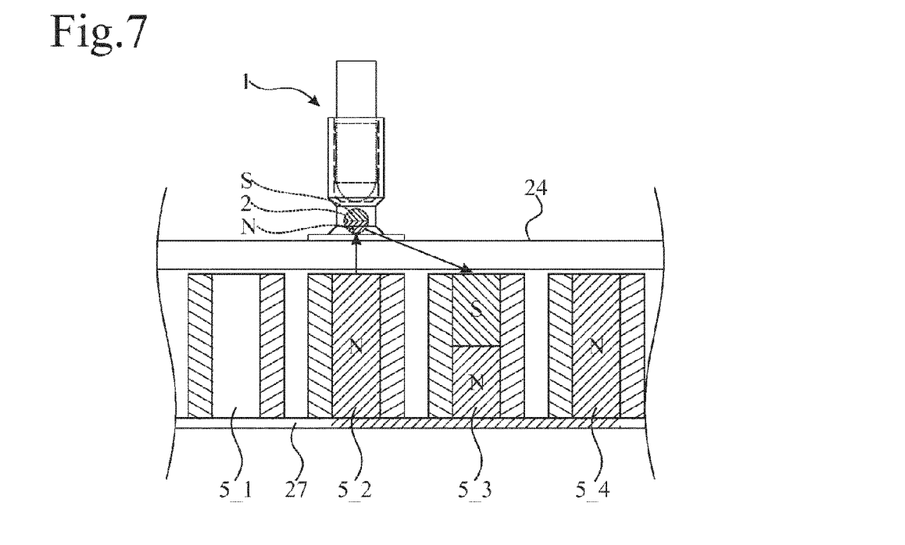
FIG. 7 illustrates a side view of an embodiment of a sub plane comprising a magnetizable coupling element providing a magnetic coupling between adjacent electro-magnetic actuators according to an embodiment of the present disclosure.

FIG. 7 shows a side view of an embodiment of a sub-plane comprising a magnetizable coupling element 27 providing a magnetic coupling between adjacent electro-magnetic actuators 5. As shown, only the electro-magnetic actuator 5_3 can be activated by driving the corresponding coil with a driving current and can cause a magnetic flow guided by the coupling element 27 and extending in the ferromagnetic cores of the non-activated electro-magnetic actuators 5_2 and 5_3. As a result, a magnetic push force can be generated by the electro-magnetic actuator 5_2 in interaction with the permanent magnet 2 reducing friction and superimposing in the desired direction with a pull force generated by the activated electro-magnetic actuators 5_3.

Figure 8:
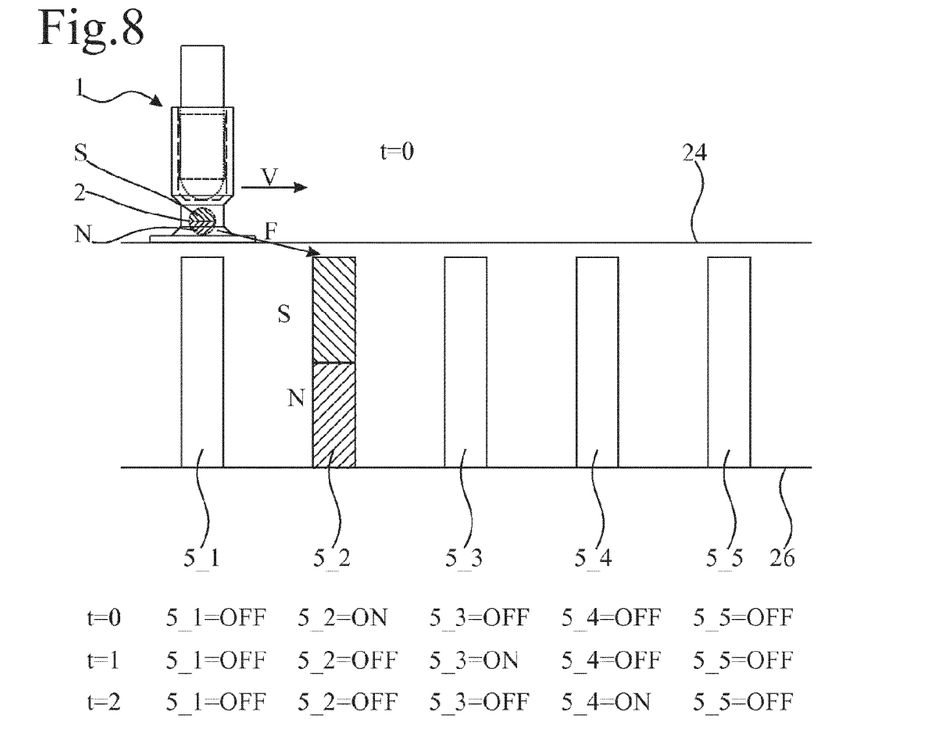
FIG. 8 illustrates movement of a container carrier and an activation order of corresponding electro-magnetic actuators according to a first embodiment of the present disclosure.

FIG. 8 shows a movement of a container carrier 1 and an activation order of corresponding electro-magnetic actuators 5_1 to 5_5 according to a first embodiment. As shown, at time t=0, only the electro-magnetic actuator 5_2 is activated such that it can generate a pull force moving the container carrier 1 in the shown direction.

At time t=1, the container carrier 1 has moved such that it can reside on top of the electro-magnetic actuator 5_2, what for example can be sensed by the container carrier sensing device. In order to continue the movement electro-magnetic actuator 5_2 can be deactivated and electro-magnetic actuator 5_3 can be activated, thereby pulling the container carrier 1 forward.

At time t=2, the container carrier 1 has moved such that it can reside on top of the electro-magnetic actuator 5_3. In order to continue the movement electro-magnetic actuator 5_3 can be deactivated and electro-magnetic actuator 5_4 can be activated, thereby pulling the container carrier 1 forward.

The above steps can be repeated as long as a movement is desired. Concluding, a group of multiple electro-magnetic actuators 5_1 to 5_5 along a transport path can be sequentially activated to move the container carrier 1 along the first transport path.

Since the electro-magnetic actuators 5 can be activated independently, it can be possible to independently and simultaneously move a plurality of different container carriers 1 along different paths wherein self-evidently collisions have to be avoided.

Figure 9:
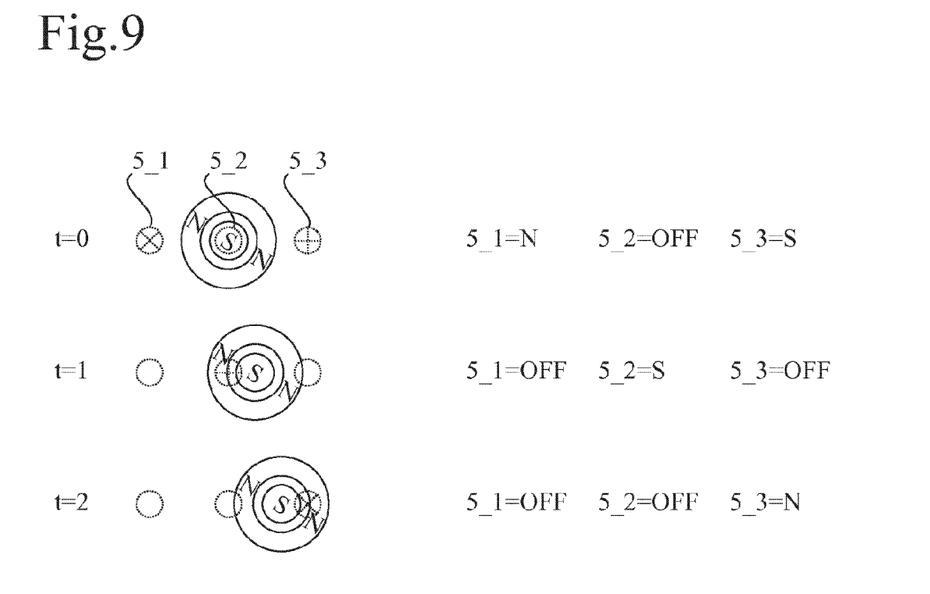
FIG. 9 illustrates movement of a container carrier and an activation order of corresponding electro-magnetic actuators according to a second embodiment of the present disclosure.

FIG. 9 shows a movement of a container carrier 1' and an activation order of corresponding electro-magnetic actuators 5_1 to 5_3 according to a second embodiment. FIG. 5 shows the container carrier 1' in more detail. In one embodiment, a movement of the container carrier 1' placed on a first electro-magnetic actuator 5_2 to an adjacent second electro-magnetic actuator 5_3 can comprise activating the first and the second electro-magnetic actuators 5_2 and 5_3 and a third electro-magnetic actuator 5_1 adjacent to the first electro-magnetic actuator 5_2 in a specific order and polarity. The electro-magnetic actuators 5_1 to 5_3 can be part of the same row or column and can be activated generating a south-pole (S) or a north-pole (N) pointing towards the container carrier 1'.

In a first step at t=0, the second electro-magnetic actuator 5_3 can be activated such that a resulting pull-force regarding the second permanent magnet 7 having a ring shape can be generated and the third electro-magnetic actuator 5_1 can be activated such that a resulting push-force regarding the second permanent magnet 7 can be generated.

After the container carrier 1' reaches a first predetermined position at time t=1, what for example can be sensed by the container carrier sensing device, the second and third electro-magnetic actuators 5_1 and 5_3 can be deactivated and the first electro-magnetic actuator 5_2 can be activated such that a resulting pull-force regarding the second permanent magnet 7 can be generated and that a resulting push-force regarding the first permanent magnet 6 can be generated.

After the container carrier 1' reaches a second predetermined position at time t=2, the first and the third electro-magnetic actuators 5_1 and 5_2 can be deactivated and the second electro-magnetic actuator 5_3 can be activated such that a resulting pull-force regarding the second permanent magnet 7 can be generated.

In one embodiment, a movement between adjacent electro-magnetic actuators 5_2 and 5_3 can be performed in a sequence of three activation patterns regarding three adjacent electro-magnetic actuators 5_1 to 5_3. This can lead to a continuous uniform smooth movement with a high positioning accuracy.

Figure 10:
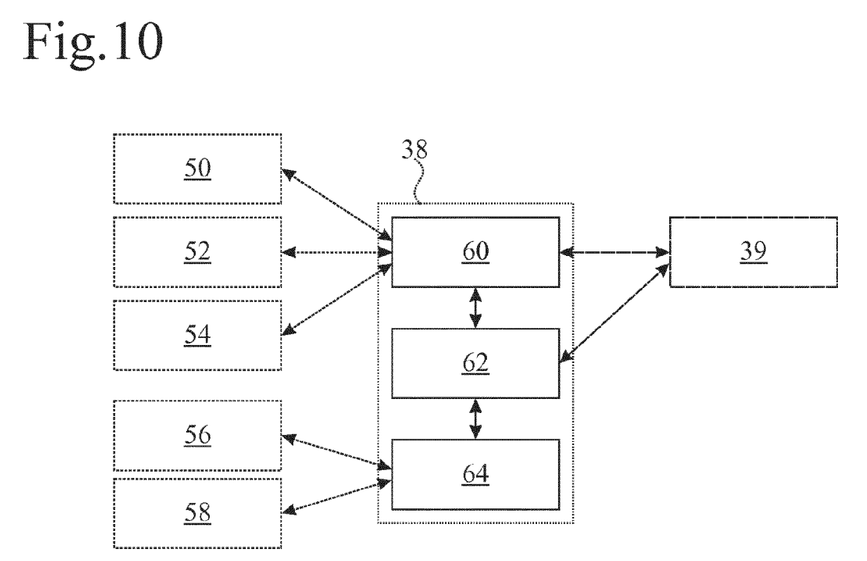
FIG. 10 illustrates a sub plane according to a further embodiment of the present disclosure.

FIG. 10 shows a block diagram of hardware architecture of the system shown in FIG. 1. The control device 38 can comprise a move unit 60, a routing unit 62 and a driver unit 64. The move unit 60 may be functionally coupled with modules 50, a barcode scanner 52 and a RFID reader 54. The move unit can control the highest level of functionality of the laboratory sample distribution system. The move unit 60 can have knowledge regarding the necessary analyses of samples processed by the system. Basically, the move unit 60 can generate start and destination locations for respective container carriers 1. Further, the move unit 60 can organize the filling of empty container carriers, the removal of samples completely processed, capping, decapping, and the like.

The routing unit 62 can compute routes based on the given start and destination points according to given criteria. Further, the routing unit 62 can generate driving commands based on the computed routes for the driver unit 64. The move unit 60 and the routing unit 62 may be coupled functionally with the visualizing device 39. The driver unit 64 may be functionally coupled with a camera 58 and driver hardware 56 directly driving the electro-magnetic actuators 5. The driver unit can control the driver hardware 56 in response to commands received from the routing unit 62.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising:
   a plurality of container carriers, wherein each container carrier comprises at least one magnetically active device and carries a sample container containing a sample; and
   a transport device comprising
      a transport plane to carry the plurality of container carriers,
      a plurality of electro-magnetic actuators stationary arranged below the transport plane, wherein the electro-magnetic actuators move a container carrier placed on top of the transport plane by applying a magnetic force to the container carrier, and
      a control device to control the movement of the container carriers on top of the transport plane by driving the electro-magnetic actuators, wherein the control device controls the movement such that two or more container carriers are movable simultaneously and independently from one another and that at least one transport section is logically defined on the transport plane and wherein container carriers are moved within the transport section in a given transport direction (r).

2. The laboratory sample distribution system according to claim 1, wherein the at least one magnetically active device is a permanent magnet.

3. The laboratory sample distribution system according to claim 1, wherein the control device controls the movement such that collisions between container carriers are avoided.

4. The laboratory sample distribution system according to claim 3, wherein the control device avoids collisions by checking if a next position on a route of a container carrier is blocked by another container carrier and if the next position is blocked, parking the container carrier on an actual position until the next position is free of container carriers.

5. The laboratory sample distribution system according to claim 1, wherein the control device controls the movement such that a route defined by a start location and a destination location is optimized by a given criteria.

6. The laboratory sample distribution system according to claim 5, wherein the given criteria is at least one of the group of:
   shortest distance between the start location and the destination location,
   transport time between the start location and the destination location,
   number of intersections with other routes,
   priority assigned to a container carrier, and
   defective electro-magnetic actuators.

7. The laboratory sample distribution system according to claim 1, further comprising,
   a container carrier sensing device to sense the presence and/or position of container carriers located on the transport plane, wherein the control device compares a scheduled position of a container carrier which has been scheduled by the control device and a sensed position of a container carrier and to generate an error message if the scheduled position and the sensed position do not match.

8. The laboratory sample distribution system according to claim 1, wherein the transport plane further comprises at least one transfer area located adjacent to a laboratory station and/or an automatic transfer device and stores a plurality of container carriers for sequentially processing by the laboratory station or the automatic transfer device.

9. The laboratory sample distribution system according to claim 8, wherein the transfer area comprises a handover position and wherein container carriers exclusively enter the transfer area by passing the handover position.

10. The laboratory sample distribution system according to claim 1, further comprising,
a visualizing device to visualize:
the presence and position of container carriers located on the transport plane, and/or
the presence and position of sample containers located on the transport plane, including information regarding corresponding samples, and/or
error conditions of the sample distribution system.

11. The laboratory sample distribution system according to claim 1, wherein the transport plane comprises at least one insertion area for manually and/or automatically inserting container carriers on the transport plane.

12. The laboratory sample distribution system according to claim 11, wherein the at least one insertion area comprises at least one priority insertion area for manually and/or automatically inserting container carriers carrying sample containers containing priority samples on the transport plane.

13. The laboratory sample distribution system according to claim 11, wherein a sensor device senses a container carrier inserted on the at least one insertion area.

14. The laboratory sample distribution system according to claim 11, wherein a bar code reader and/or a RFID reader reads a barcode and/or RFID tag information identifying a sample container comprised in a container carrier inserted on the at least one insertion area.

15. The laboratory sample distribution system according to claim 1, wherein the transport plane comprises at least one removal area for manually and/or automatically removing container carriers and/or sample containers from the transport plane.

16. A method of operating a laboratory sample distribution system according to claim 1, the method comprising:
controlling the movement of the container carriers on top of the transport plane by driving the electro-magnetic actuators such that more than two container carriers are movable simultaneously and independently from one another.

* * * * *